US008673153B2

(12) United States Patent
Campagnolo et al.

(10) Patent No.: US 8,673,153 B2
(45) Date of Patent: Mar. 18, 2014

(54) METHOD AND DEVICE FOR DIVISION OF A BIOLOGICAL SAMPLE BY MAGNETIC EFFECT

(75) Inventors: Raymond Campagnolo, Grenoble (FR); Christian Jeandey, Saint Egreve (FR); Frederic Ginot, Saint Egreve (FR); Patrick Pouteau, Meylan (FR)

(73) Assignees: Commissariat a l'Energie Atomique, Paris (FR); Biomerieux SA, Marcy l'etoile (FR)

( * ) Notice: Subject to any disclaimer, the term of this patent is extended or adjusted under 35 U.S.C. 154(b) by 1164 days.

(21) Appl. No.: 10/581,357

(22) PCT Filed: Dec. 13, 2004

(86) PCT No.: PCT/EP2004/053411
§ 371 (c)(1), (2), (4) Date: Jun. 2, 2006

(87) PCT Pub. No.: WO2005/059085
PCT Pub. Date: Jun. 30, 2005

(65) Prior Publication Data
US 2007/0199901 A1  Aug. 30, 2007

(30) Foreign Application Priority Data
Dec. 15, 2003 (FR) .................................... 03 51059

(51) Int. Cl.
*B03C 1/02* (2006.01)
(52) U.S. Cl.
USPC ............ 210/695; 210/222; 436/177; 436/526
(58) Field of Classification Search
USPC .......... 210/222, 223, 695; 422/502, 504, 513, 422/534, 552, 507; 436/177, 526; 209/214, 209/225, 226, 227
See application file for complete search history.

(56) References Cited

U.S. PATENT DOCUMENTS

| | | | | |
|---|---|---|---|---|
| 2,258,194 A | * | 10/1941 | Queneau | 209/232 |
| 3,770,027 A | | 11/1973 | Guigan | |
| 4,526,681 A | * | 7/1985 | Friedlaender et al. | 209/214 |
| 4,663,029 A | | 5/1987 | Kelland et al. | |
| 4,910,148 A | | 3/1990 | Sorensen et al. | |

(Continued)

FOREIGN PATENT DOCUMENTS

| | | |
|---|---|---|
| EP | 0 136 126 | 4/1985 |
| EP | 0 496 200 | 7/1992 |

(Continued)

OTHER PUBLICATIONS

Office Action issued Jun. 22, 2010 in Japanese Patent Application No. 2006-544421 (with partial English Translation).

*Primary Examiner* — David C Mellon
(74) *Attorney, Agent, or Firm* — Oblon, Spivak, McClelland, Maier & Neustadt, L.L.P.

(57) ABSTRACT

A method for dividing an analyte present in a solution and that is fixed on magnetic particles, and devices to be used in the method and systems for implementing the method. The method includes sedimentation of the magnetic particles together with separation into a plurality of residues. One implementation: forms at least a residue of magnetic particles in a first receptacle; and displaces the at least the residues towards a plurality of second receptacles, preferably by relative translation of a magnetic system. The second receptacle is connected to the first receptacle through a fluid channel.

12 Claims, 6 Drawing Sheets

(56) References Cited

U.S. PATENT DOCUMENTS

| | | | |
|---|---|---|---|
| 5,567,326 A | 10/1996 | Ekenberg et al. | |
| 5,628,407 A * | 5/1997 | Gilbert et al. | 209/214 |
| 5,795,470 A | 8/1998 | Wang et al. | |
| 5,925,573 A * | 7/1999 | Colin et al. | 436/525 |
| 6,013,188 A * | 1/2000 | Terstappen et al. | 210/695 |
| 6,013,532 A | 1/2000 | Liberti et al. | |
| 6,036,857 A | 3/2000 | Chen et al. | |
| 6,342,396 B1 * | 1/2002 | Perrin et al. | 436/518 |
| 7,015,047 B2 * | 3/2006 | Huang et al. | 436/526 |
| 2002/0084225 A1 | 7/2002 | Hatch et al. | |
| 2002/0137226 A1 * | 9/2002 | Tanaami | 436/149 |
| 2003/0044832 A1 | 3/2003 | Blankenstein | |
| 2004/0023273 A1 | 2/2004 | Puget et al. | |
| 2004/0043507 A1 * | 3/2004 | Song et al. | 436/514 |
| 2006/0024732 A1 * | 2/2006 | Huang et al. | 435/6 |

FOREIGN PATENT DOCUMENTS

| | | |
|---|---|---|
| EP | 1 179 585 A2 | 2/2002 |
| JP | A 2001-221799 | 8/2001 |
| WO | 94 26414 | 11/1994 |

* cited by examiner

FIG. 9 though the invention relates to the use of magnetic means to divide the analyte that was previously fixed on magnetic particles.

METHOD AND DEVICE FOR DIVISION OF A BIOLOGICAL SAMPLE BY MAGNETIC EFFECT

TECHNICAL FIELD

This invention relates to a method for equitable or non-equitable division of an analyte present in a sample, and to a device and a system for implementation of this method.

More particularly, the invention relates to the use of magnetic means to divide the analyte that was previously fixed on magnetic particles.

STATE OF PRIOR ART

An analyte means all or part of a corpuscle or molecule to be isolated and/or to be moved into another medium so that it can be used and/or demonstrated, such as a micro-organism, a bacteria, a fungus, a virus, an eukaryote cell; a chemical compound; a molecule such as a peptide, a protein, an enzyme, a polysaccharide, a lipid, a lipoprotein, a lipopolysaccharide, a nucleic acid, a hormone, an antigen, an antibody, a growth factor, a hapten; a cell such as a tumoral cell, etc.

This invention is applicable to all fields in which there is a need for making treatments in parallel on a single sample, for example in the case in which treatments are mutually exclusive or have to be done in solutions incompatible with each other.

Thus, in some in vitro diagnostic tests, it is desirable to carry out a number of PCR type amplifications on an initial sample; these different amplifications frequently require different primers, different thermal conditions and different buffer components to optimise the amplification.

Similarly, during immunological tests, a number of different ligands have to be tested with an initial protein; a single species present in the sample is subjected to a number of reactions for antibody/antigen recognition.

It should be noted that these applications require a division which is equitable or non-equitable of a phase of the medium, rather than separation of this medium into several phases.

One of the simplest solutions for dividing a sample present in the liquid phase into a number of sub-samples consists of taking a sub-volume of the initial volume and adding it into a receptacle in which one of several specific reactions to be carried out on the analyte will be done.

This solution has an obvious limitation in terms of the smallest manipulable volume of the order of a few microlitres, with a precision of the order of 1%. For lower contents, liquid is lost, and therefore analyte is lost by transporting it in "large" receptacles such as pipette cones, flasks, etc. Other problems that arise are evaporation and adsorption problems on receptacle walls during these manipulations. This solution also requires manual or automatic liquid transfers leading to an inevitable reduction in the quantity of analysable analyte and a dilution of the analyte until a division quite different from the initial planned division is made; in the case of a weak concentration of analyte in the initial sample, this can cause total disappearance of the analyte or a reduction of its quantity such that it becomes undetectable.

Another solution consists of filling a single receptacle containing a switching device provided with valves, leading to the sub-receptacles. Placement of these valves becomes complex and occupies a considerable amount of space whenever the number of sub-receptacles exceeds a few units.

Therefore there is a real need for a method and a device for equitably or non-equitably dividing an analyte to transport it from an initial receptacle into a number of second receptacles without fluid manipulation and with good efficiency. For the purposes of this invention, transport of the analyte means displacement of the analyte from one receptacle to another, with or without the liquid medium in which it is present.

SUMMARY OF THE INVENTION

This invention satisfies this need, among other advantages.

According to one of its aspects, the invention relates to a method for division of an analyte present in a solution in a first receptacle, and fixed onto magnetic particles. Particles are settled by first magnetic means and the analyte is distributed into several residues located in second receptacles.

According to one embodiment, the magnetic particles are settled into at least one residue in the first receptacle, a derived residue being displaced to second receptacles by second magnetic means. Advantageously, the second magnetic means, and/or the magnetic field created by these second magnetic means, is displaced relative to the first receptacle. Preferably, the same magnetic means are used to settle and to displace the residue, in other words the first and second magnetic means are coincident in a single entity.

The second receptacles are connected to the first receptacle, each through a fluid channel, and are filled with a solution that may be identical or not, and that is similar or not to the solution in the first receptacle.

Therefore, the division method avoids any pipetting and displacement of the solution as such; this enables greater precision making it possible to work on smaller volumes. The method also provides a means of making the division at the same time as the analyte is transferred from the initial solution to another solution necessary for the analyses, if this is the case.

Advantageously, each second receptacle is connected to the first receptacle through a single fluid channel, but it is possible that the second receptacles are connected to each other through a different number of channels. The control over the layout of the channels determines the quantity of analyte in each second receptacle. Thus, the arrangement of identical channels in parallel with exactly the same spacing between each channel makes it easy to have an equitable division method.

According to one preferred variant of this embodiment, a single linear residue is formed, the size of which is identical to the size of the first receptacle that it therefore passes through; one possibility is to use a long magnet or an elongated induction coil, for example. The residue is then moved, possibly by relative displacement of the coil or the magnet with respect to the device. Therefore, the relative translation of the linear residue and possibly the magnet, "scavenges" the first receptacle and breaks the residue into sub-units depending on the inlet area to the fluid channels; for example, if all channels are identical and are located on the same side of the centre line along which the residue is formed, the division will be equitable. Advantageously, the magnet or the induction coil are larger than the first receptacle such that they "project beyond" the surface of the first receptacle, thus enabling complete and uniform transport of magnetic particles and fast magnetic sedimentation. In preference, these magnetic means move perpendicular to the channels.

One alternative is displacement of the magnetic field without physical displacement of the magnetic means, for example with magnetic means comprising successive coils.

The main advantages of this variant in which a division of a formed residue takes place, are the simplicity of its use and that no precise alignment between the magnetic structure and the fluid structure is necessary.

According to another variant of the same embodiment, a residue with smaller dimensions is formed facing each channel. For example, a multi-tip magnetic structure could be used, which translates each residue into the corresponding channel.

Advantageously, the fluid channels are connected to the first receptacle through a neck that enables a transition for the flow of magnetic particles and better control over the transported quantity. For an equitable division, the necks are identical for each channel.

The channels may be capillaries. One or more magnetic tracks could also be created to guide the magnetic particles. Advantageously, for small samples, magnetic tracks can replace the channels.

Magnetic particles may be transported as far as the second receptacles, where a process to release the analyte takes place, or the release can occur before arrival of the analyte in the second receptacles, subsequent transport of the analyte possibly being made by liquid displacement.

According to another embodiment, the sedimentation of magnetic particles coupled to analytes and present in solution in the first receptacle is done directly in a plurality of second receptacles. In this case, the second receptacles may be formed entirely with the first receptacle, advantageously without an area (such as a plane surface) in which the particles could be immobilised outside the second receptacles.

The analyte can be fixed on magnetic particles before the solution is added into the first receptacle, or the solution can be added and fixation can be done in the receptacle.

The invention also relates to a device for division of an analyte fixed on magnetic particles, comprising several second receptacles connected to a first receptacle, for example through fluid channels. Preferably, the entire fluid circuit will be in one support that may be either the base or the cover of the device. Advantageously, inlet means are connected to the support.

These devices may form part of systems according to the invention that include magnetic means, possibly movable and particularly capable of being subjected to a relative translation with respect to a transport or division device, and that entrain magnetic particles from the first receptacle to the second receptacles of the device. One alternative relates to means that can generate a mobile field.

Preferred embodiments of devices and systems are a direct result of the corresponding advantages compared with division methods.

BRIEF DESCRIPTION OF THE DRAWINGS

Other characteristics and advantages will become clear after reading the following examples that are obviously given for illustrative purposes and are in no way limitative, with reference to the attached figures.

In these Figures, identical references refer to identical elements.

DETAILED DESCRIPTION OF PARTICULAR EMBODIMENTS

Figure 1:
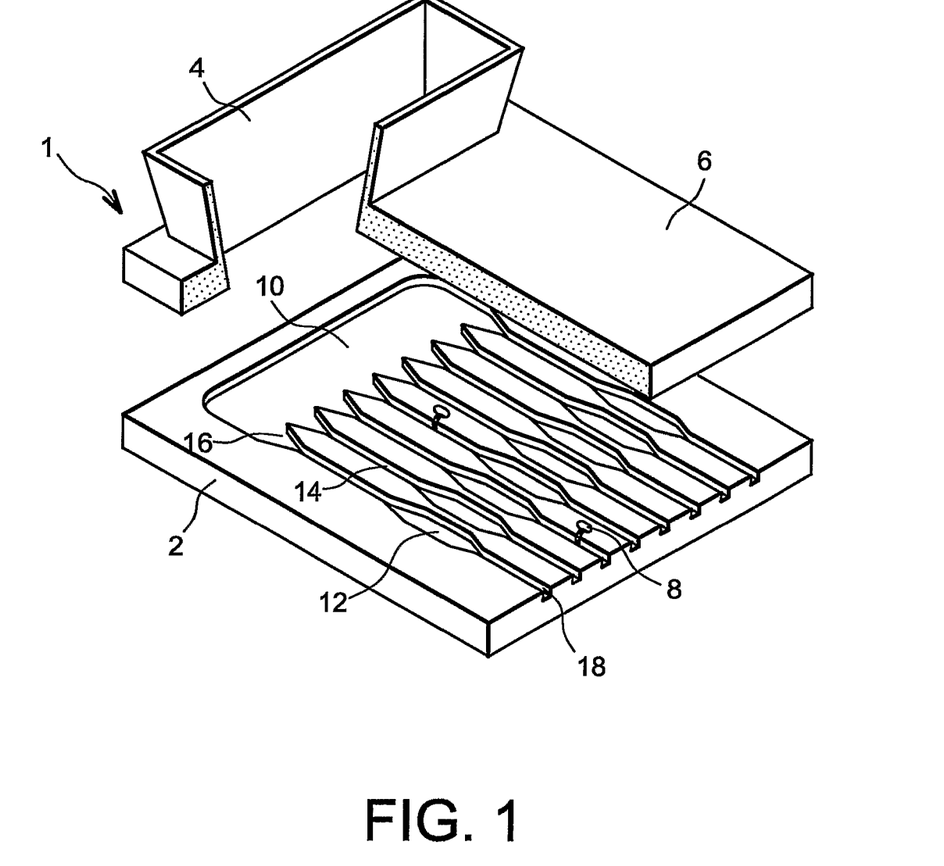
FIG. 1 shows a perspective and exploded diagrammatic view with a partial section through a first embodiment of a device according to this disclosure.

The general architecture of a device 1 according to a first embodiment of the invention is shown in FIG. 1. It is composed of a base 2, possibly prolonged by inlet means 4 and a cover 6. An inlet chamber (or first receptacle) 10 is located on the base 2 and is connected to reaction chambers (or second receptacles) 12 through fluid channels 14 provided with a neck 16, in this case in the form of capillaries. The bottom of the fluid channels 14 may be covered by a ferromagnetic strip.

The particular shapes of the chambers 10, 12 are given as example; the receptacles and the capillaries may have other shapes and/or sizes and may be different from each other depending on the application or the technology used for manufacturing the device 1. Similarly, there may be several fluid channels 14 connecting the first chamber 10 to a single reaction chamber 12. Furthermore, other elements necessary for the reactions can be included within the fluid circuit; for example, it is possible to include bubble valves 8 along capillaries 14 or on the second receptacles 12.

FIG. 1 suggests a manufacturing method by which the device 1 is made by etching the receptacles 10, 12 and fluid channels 14 in a plane material acting as a base 2, and then assembling the cover 6 by gluing or any other attachment means. This is one possible manufacturing method, but the invention is not dependent on it. Any other technology for making an inlet chamber 10 connected to several reaction chambers 12 through one or several fluid channels 14 could be envisaged. In particular, possible methods that could be envisaged for integration of the fluid circuit onto a support include etching on silicon or glass, micro-injection, hot stamping, plasma etching techniques, techniques similar to the "LIGA" technique using lithography, galvanoplasty and plastic moulding. Etching is preferable for depths of the order of 100 μm.

It is also possible to etch the cover 6 instead of the base 2.

Figure 8:
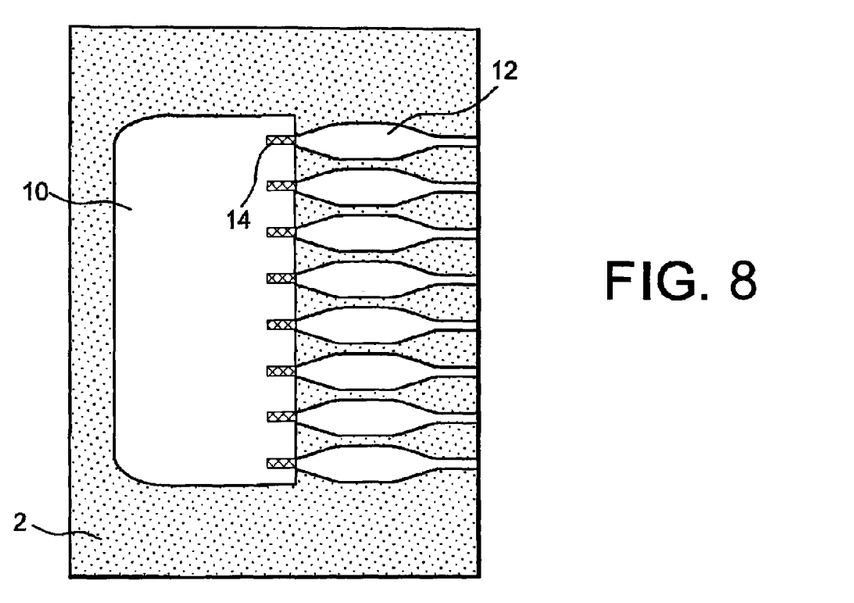
FIG. 8 illustrates a diagrammatic view of magnetic strips forming magnetic guide channels of a device according to this disclosure.

It may be advantageous to not use "physical" channels 14, but simply ferromagnetic or magnetic strips deposited on the bottom of the base 2 that will guide the magnetic particles like etched channels. An exemplary implementation of magnetic strips 80 forming "non-physical, " magnetic guide channels 14 is illustrated in FIG. 8. This provides greater freedom in the trajectory of the residue, the particles being guided by the ferromagnetic/magnetic tracks; furthermore, the presence of magnetic strips eliminates surface condition problems in fluid chambers.

Figure 9:
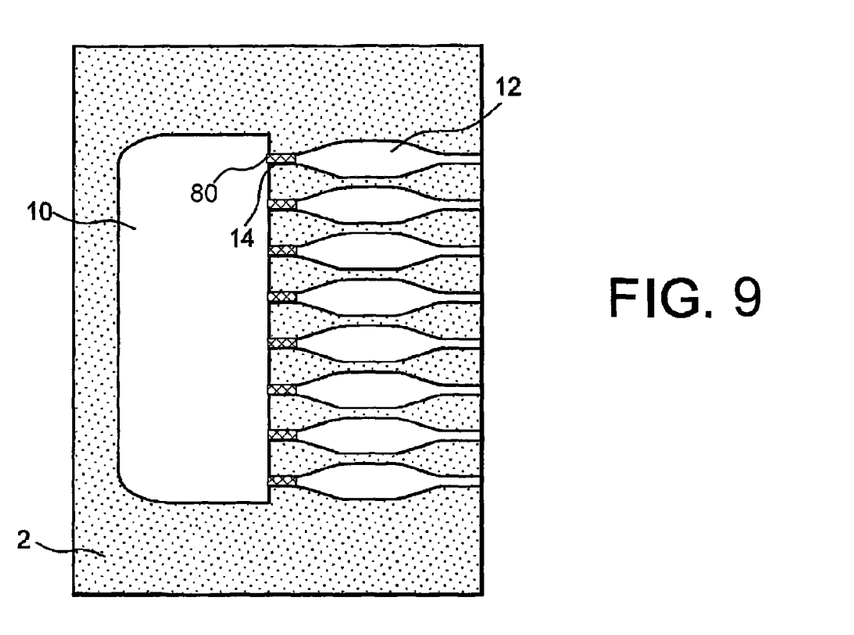
FIG. 9 illustrates a diagrammatic view of magnetic strips deposited at the bottom of physical channels of a device according to this disclosure.

These two techniques ("physical" channels and magnetic guide channels) can also be combined, and a magnetic strip can be deposited at the bottom of each "physical" fluid channel 14, depending on how the device is used. FIG. 9 illustrates an exemplary implementation of magnetic strips 80 deposited at the bottom of each "physical" fluid channel 14.

A vent 18 is used for evacuation of fluids (air or liquid) when liquids are filled or transferred in receptacles. It may be used when the device is being filled to evacuate the gases present, as well as in the final step to recover the analyte solutions, but a vent is not essential.

The sample and the different reagents or buffers can be added into the devices in different ways. For example, in a first variant shown in FIG. 1, the cover 6 of the device is fitted with inlet means in the form of a conical dish 4; it is obvious that this shape is only given as an example. For example, by applying a pipette or a syringe end piece onto this conical dish, the buffer or a reagent can be "pushed" inside the device by applying a pressure on the liquid. Air or any other fluid (liquid or gas) present in the device will be evacuated from the device through the vents 18. In this case, these vents open up into the reaction chambers 12, but they could be placed in other locations of the device 1 depending on the case.

Another variant (not shown) for adding liquid into the device would consist of adding it through a channel or capillary similar to the vents 18 opening up into the first chamber 10, and itself connected to the outside of the device through an interface.

The first step in using the device 1 is to prepare a homogenous solution containing the analyte according to known techniques; for example, the analyte is extracted from the sample in which it is contained, or "pure" analyte is directly diluted in solution.

The analyte is then fixed on magnetic particles. The size of magnetic particles is appropriate for the analyte to be isolated and the solution volume. For example, they may be sub-micrometric in size when the analyte is a molecule. The quantity of particles used depends particularly on the nature and quantity of analyte to be fixed, and is preferably provided in sufficient numbers to fix the entire analyte. In general, appropriate magnetic particles are conventionally used in molecular and cellular biology. If possible, in particular they must be superparamagnetic so that they can be spontaneously rediffused after the magnetic field has been cancelled. These particles form part of the magnetic colloids family and are polymerised and functionalised by the bond with a number of antibodies.

Fixation methods are known to those skilled in the art; adsorption, coalescence, capture by nucleotides present on the particle surface, thermosensitivity.

It is preferable that this fixation should be reversible; it may be necessary to release the analyte so that it can access chemical reagents or detection means more easily, or be more easily accessible to them. Those skilled in the art are familiar with release of the analyte, or elution.

The fixation step may precede the addition of the solution into the first receptacle 10, but it may also take place in this receptacle; the solution is then added into the receptacle in which magnetic particles are also present.

Before the analyte is added, the device 1 is filled with buffer without the analyte searched for and without magnetic particles. This buffer may be added by pouring the necessary quantity into the inlet means 4, and by applying a pneumatic pressure on it. Once the device has been filled, the excess buffer present in the inlet means 4 may be removed, for example using a pipette. The second receptacles 12 can be filled with a solution different from the buffer in the inlet chamber 4, 10, and even a different solution can be used in each chamber 12 depending on how the device is used and on the planned analyses.

The sample, composed of a given quantity of buffer in which interesting analytes have previously been fixed on magnetic particles, is deposited in the first receptacle 10. This sample is considered as being single phase; the analyte to be transported and divided is present in a one phase.

As described above, magnetic particles can be placed in the first receptacle, and analytes in solution can then be added into the buffer to fix them on the particles.

In this first embodiment, the magnetic particles are then attracted to the bottom of the inlet chamber 10 in the sedimentation step. Preferably, sedimentation is done using (first) magnetic means; particles are generally micrometric or even nanometric in size, and the magnetic means can increase the sedimentation rate compared with a natural sediment.

The sedimentation rate of fixed size magnetic particles depends on the distance of the particles from the top face of a magnetic block located under the receptacle containing the particle solution, and also the volume of the block.

In the context of the embodiment presented in the following figures, the residue is formed using the first magnetic means represented by the magnet 20 that will also be used for displacement of the residue 22, and which is in the shape indicated in FIG. 2. It is positioned under the device 1, vertically below with the conical dish 4 in the case illustrated. The magnetic particles are then collected in a linear residue 22 passing through the first chamber 10, along a line AA. However, and as already described, the first magnetic means may have been used only to settle particles in an initial residue, possibly the same shape as this residue 22, the displacement being achieved by second different magnetic means. In this case, the second magnetic means 20 may have rearranged the first residue.

According to one preferred embodiment, the residue 22 is displaced by the relative displacement of the first magnetic means, coincident with the second magnetic means as will be described in detail later; a relative displacement of this type can control displacement of the residue and uniformity of the applied magnetic field. However, other solutions could be envisaged, for example a powerful fixed magnet located in the direction of the second receptacles and attracting the residue 22. If a coil is used instead of the magnet, the displacement of the coil may thus be replaced by switching between successive coils in an assembly provided for this purpose; there is then a relatively displacement of the magnetic field, with the physical magnetic means remaining in position. Combinations are possible.

Advantageously, this long magnet 20 "projects beyond" from the first receptacle 10. During the movement, the magnet 20 thus scavenges the entire receptacle 10 located at its right, in other words in the direction of the movement (arrow). In fact it is preferable if it is longer than the linear residue 22, and if possible as long as the displacement. Therefore in general, it is desirable that the length of the magnet 20 should be such that, at all times during the relative displacement of the magnet, projection of the width of the first receptacle onto a plane containing the magnet (for example in this case the horizontal plane) and along the plane orthogonal to the displacement (in this case the vertical plane passing through the AA axis) is included within the magnet, or the segment represented by the magnet; the width of the receptacle 10 is defined by the widest segment derived from intersection of the vertical axis and the linear residue 22 that passes through the first receptacle 10.

Figure 2:
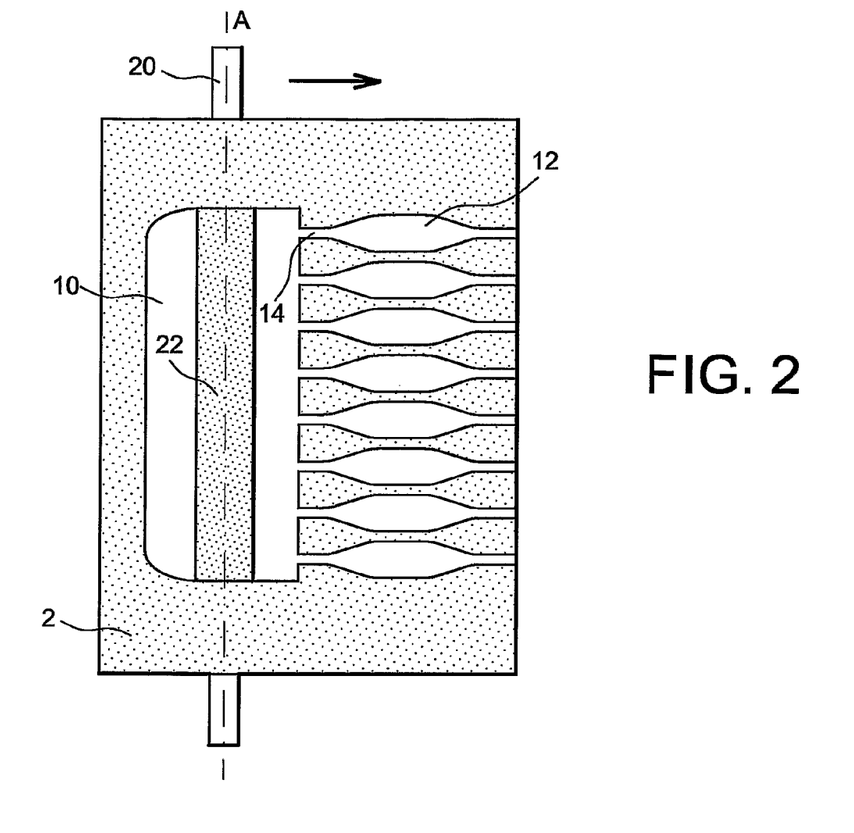
FIG. 2 shows a diagrammatic view of the formation of a residue according to a first embodiment of the division system according to this disclosure.

It should also be noted the lack of a neck 16 in FIG. 2; the "comb" shaped structure may be advantageous to better control the division.

Figure 3:
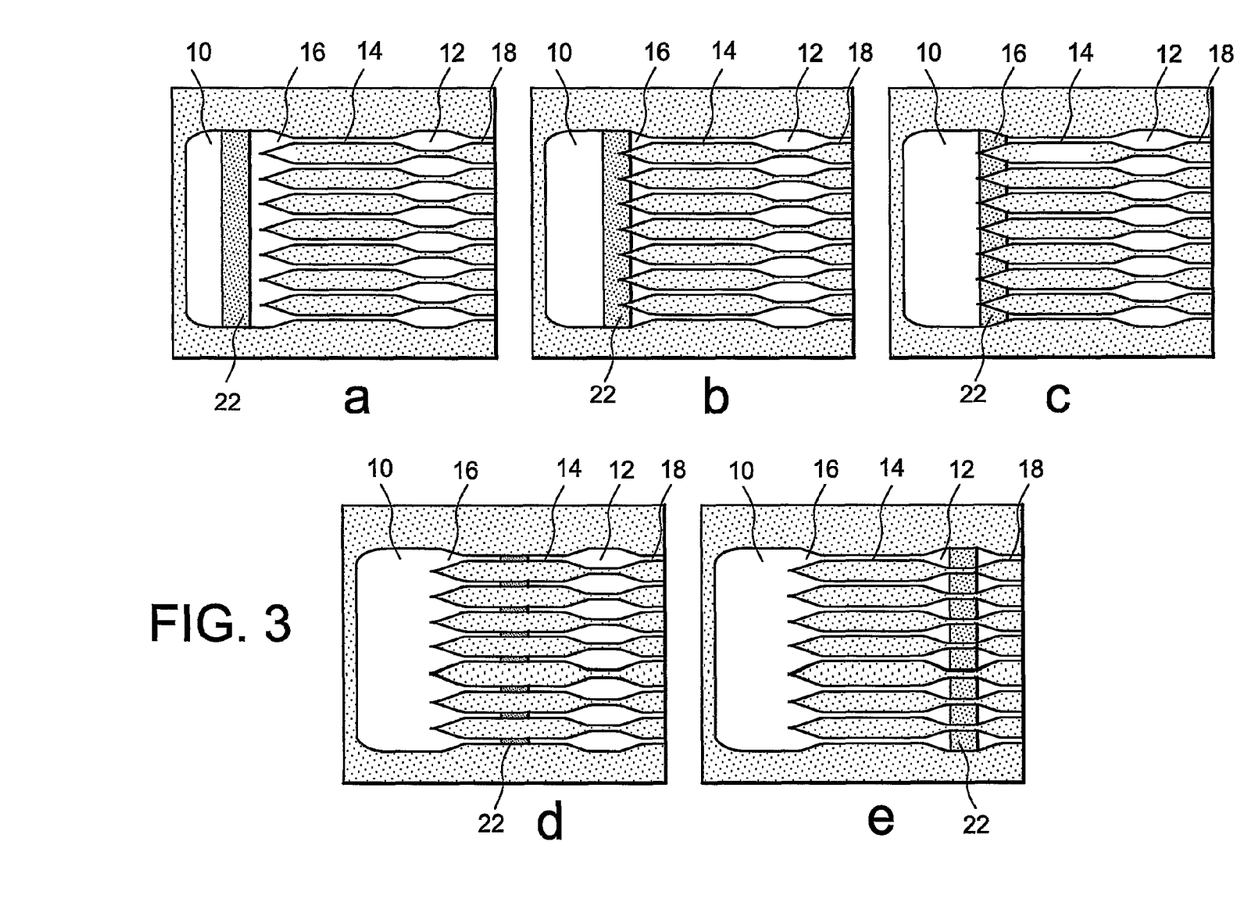
FIG. 3 shows a diagrammatic view of the division method according to one embodiment of this disclosure.

FIG. 3 represents the division of the residue and therefore the analyte by displacement of the residue 22 from the first receptacle 10 to the second receptacles 12. FIG. 3a shows the configuration of FIG. 2 and therefore describes a linear residue 22, this residue being the result of rearrangement of particles by second magnetic means.

It is desirable in this embodiment that all fluid channels should be located on the same side of the AA axis shown by the residue 22. Otherwise, as will be better understood after reading the following, translation of the residue would imply non-filling of the reaction chambers 12 located on the other side of the translation direction.

The initial residue is "guided" to fluid channels 14 due to relative displacement, in this case in translation, of the magnet 20 towards the second chambers 12; see FIG. 3b. Relative displacement means either physical displacement of the magnet 20 (or the generated field) that can be moved by any mechanism whatsoever, or manual movement under the support 2-6 or displacement of the support 2-6, for example along a rail above the magnet 20. For example, it is worth mentioning the use of a stepping motor or a pneumatic jack as translation means, but any displacement means known to those skilled in the art could be envisaged depending on the case.

Due to the relative translation of the magnetic means or the magnetic field, it is found that the residue maintains its linear structure during its displacement.

The residue 22 thus reaches the inlet of fluid channels 14, in which the function of the walls is to separate it into segments (see FIG. 3c). Translation of the residue 22 continues along the fluid channels 14 (FIG. 3d) so that the samples reach the second receptacles (or reaction chambers) 12 (FIG. 3e).

In the example shown in FIG. 3, the fluid channels 14 are parallel to each other and perpendicular to the axis of the residue 22, the relative displacement of the magnet being parallel to the direction of the channels. These two elements are preferred since control of the location of the analyte in the channels and the reaction chambers is easier. However, other possibilities could be envisaged (oblique magnet and/or divergent channels, and/or oblique displacement, etc.).

Figure 4:
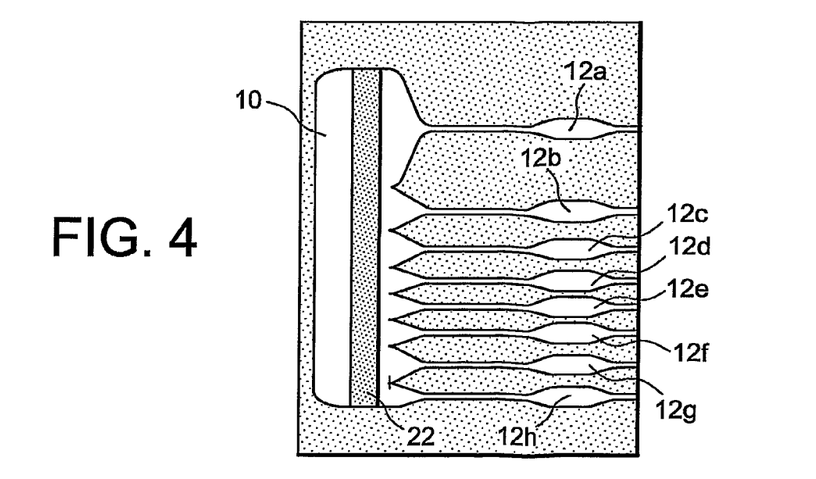
FIG. 4 shows a diagrammatic view of a second device according to this disclosure.

Furthermore, the division presented in FIG. 3 is equitable, in other words each of the second receptacles 12 receives the same quantity of analyte, and the initial analyte was divided into equal parts, in this case eight parts. In particular, the pitch between the channels 14 is constant and the necks 16 have exactly the same size. However, a modification of the layout of fluid channels provides a means of making non-equitable but controlled divisions. FIG. 4 shows such an example in which the second receptacles 12a-h do not each contain one eighth of the quantity of the initial analyte; the chamber 12a will receive almost a third of the analyte quantity, which is three times more than chambers 12d-f for example, separated by a constant pitch, in which the contents will be identical in each.

Another variable relates to the number of fluid channels opening up in a single reaction chamber 12; for a channel layout similar to that shown in FIG. 3, if two channels join each other in a first chamber 12 while each of the others opens up in an independent chamber, this first chamber 12 will receive twice the amount of analyte as the others.

Therefore, the method according to the invention enables controlled non-equitable divisions, before the liquid itself is manipulated. For example, it would be possible to create kits in which reagents are already placed in the reaction chambers 12 by any known means, and for which the layout of the channels 14 and therefore the division coefficients have been defined as a function of reaction sensitivities. Such kits could also be created for equitable divisions.

Instead of using a long magnet and a linear residue for the displacement, according to another variant, it would be possible to directly reform a number of residues corresponding to the number of fluid channels 14. For example, a magnetic structure with multiple projections 24 could replace the long magnet 20 for a device like that shown in FIG. 2.

Figure 5:
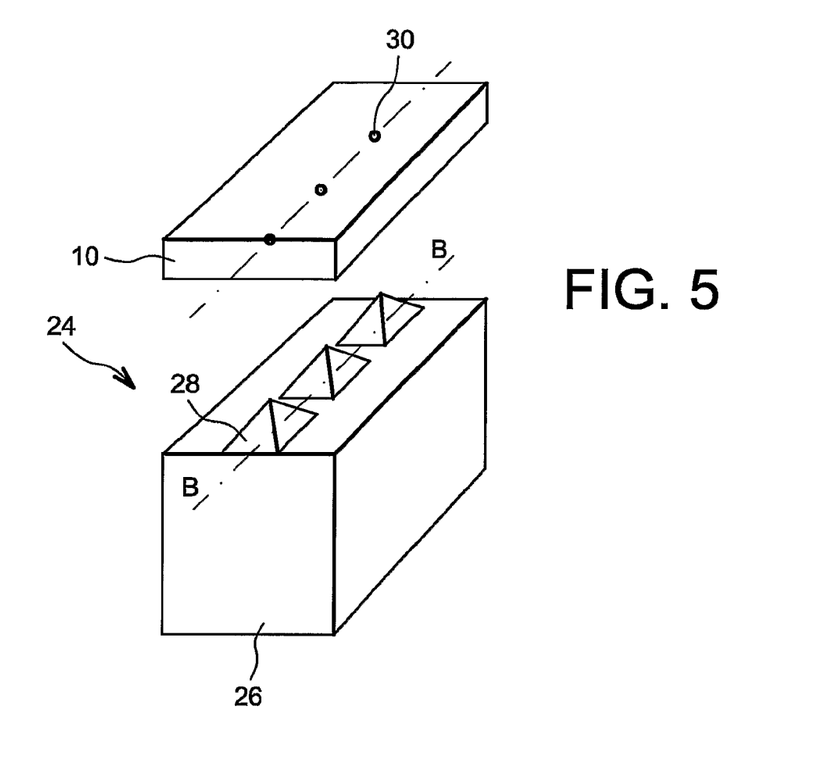
FIG. 5 shows a diagrammatic view of a multi-tip magnetic structure and its action.

A device with multiple projections 24 consists of a magnetic block 26 for which the top face is preferably cut, so as to obtain "tip" or pyramid shaped projections 28; see FIG. 5. It would also be possible to add a polar part made of a ferromagnetic material (iron, iron-chromium alloy such as the AFK502 alloy by Imphy SA) comprising tips preferably machined in the form of pyramids 28 on the plane surface of a magnetic block. The role of the tips 28 is to curve the trajectory of the magnetic particles at the end of their sedimentation; the influence of the block 26 is overriding until particles in solution are separated from the tips by two to three times the height of the tips, and sedimentation is uniform. Then, as the particles become closer to the bottom of the first receptacle 10 and therefore to the surface of the magnetic block 26, there is an increase in the relative influence on them due to the magnetised protuberances materialized by the tips 28. Therefore the residues 30 themselves are located above the tips 28.

In FIG. 5, only a few separate tips are shown for convenience, but it is quite clear that they could also form a denser network. Similarly, although in this case they are aligned along a BB axis, in some applications it would be possible to form a "checkerboard" network, for example, with several projecting lines BB or any other appropriate geometry.

Although a reduction in scale does not theoretically affect the magnetic properties (the value of the field is kept), however magnetic forces proportional to the gradient of the magnetic field are modified; since they are applied in a small volume, they are increased in a ratio inverse to the dimensions. Therefore the choice of dimensions and material for the magnetic system depends on usage conditions.

There is no limitation in the production of large magnetic blocks; up to a few tens of centimetres, for example with 13 tips at a pitch of 5 mm over a length of 65 mm. Since the sedimentation rate depends on the volume of the magnetic block, a uniform sedimentation can be obtained by advantageously using a block 26 with a surface area greater than the surface area of the first receptacle 10 of the analyte solution.

Another example embodiment is a 15×40×25 mm NdFeB block with 6 pyramids with a square cross-section with a 5 mm side and height of 2 mm. This model has excellent performances, particularly with a liquid height in the first receptacle 2 equal to 5 mm.

In particular, for a first receptacle 10 with a 3 mm section and a 4 mm depth, one of the preferred embodiments consists of having a distance equal to about 1 mm between the bottom of the first receptacle and the top of the magnetic block, in other words between the residue of magnetic particles 30 and the top of the tip(s) 28.

In practice, the dimension of the magnetic block 26 may homothetically reduced with no difficulty to areas as small as the order of 100 square millimetres. For smaller dimensions, the tips should be machined from a soft magnetic material with a strong magnetisation at saturation, such as pure iron or an $Fe_{50}Co_{50}$ alloy.

For even smaller areas (with sides of the order of 100 μm), microelectronic processes such as surface nickel plating are used; the parallelepiped shaped block can be used to magnetise (polarise) the deposits. This embodiment in particular may be combined with the use of magnetic tracks; the shape of the deposits may for example consist of concentration pads connected to the reaction chambers 12 through tracks, the deposited materials preferably being coated with a protection layer.

Like the long magnet 20, the magnetic means with projection(s) 24 enable transport of residues 30, by relative displacement, for example a relative translation along the channels, in this case small residues, in each channel.

Unless this variant is combined with magnetic tracks, it is suited more particularly for operation with larger devices with a pitch between residues 30, and therefore between channels, of more than one millimetre. In this way, a fairly accurate alignment can be achieved between the magnetic structure and the fluid structure. However, it can be used to divide an initial solution with a lower concentration, depending on the density of tips 28. Moreover, since the separation is made in the absence of the mechanical separation device, the magnetic particles are not likely to be collected on a wall of the separator.

Figure 6:
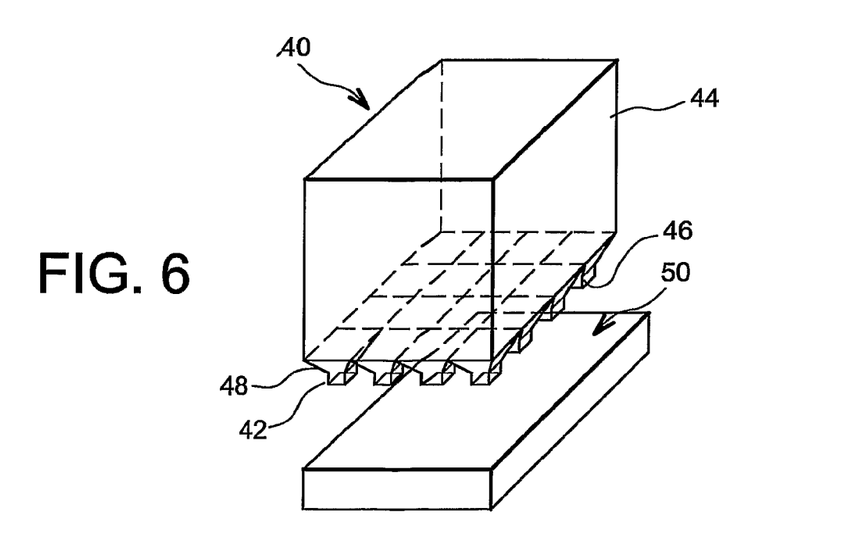
FIG. 6 shows another embodiment of the division device according to the disclosure.

Another embodiment of a device 40 by which it is possible to proceed according to the invention is shown in FIG. 6. As can be seen in this case, the fluid channels actually correspond to communications enabling the fluid to pass; the second receptacles 42 appear as direct prolongations of the first receptacle 44. The device 40 may actually be a single part including a wall 46 that may be moulded or stamped, etc., to create the second receptacles 42; this wall 46 may also be added onto a composed receptacle. Although it is not essential, it is desirable that the transition should take place gradually due through necks 48; it is also possible that each of the second receptacles 42 should be composed of a cone. In particular, it is preferable that there are no plane areas on the wall 46 of the first receptacle 44 on which the projections are arranged representing the second receptacles 42.

The division can then take place directly during sedimentation; the first magnetic means 50 located under the surface 46 attract the magnetic particles in solution into the first receptacle 44, and residues are formed in each of the second receptacles 42, consequently leading to a division of analytes present in the initial sample.

For this embodiment, the force of the magnet 50 is homogenous if possible, at the second receptacles 42. The manufacture of the device 40 and control mechanism of the magnet 50 are simpler than in the embodiments described above.

FIG. 6 shows an embodiment in which the magnet is located under the device 40. This embodiment is preferred because it uses gravity in parallel, but it is possible to have a similar device for which the surface 48 provided with projections forming the second receptacles 42 is not located on the base. Similarly, the arrangement shown is only illustrative, and sedimentation can be done with a magnet with a shape different from the block 50 (for example projections under each second receptacle 42).

As described above, sedimentation into several residues in the second receptacles 42 may also be followed by transport of the analyte from these second receptacles along a fluid path (not shown) in order to make an analysis.

Therefore according to the invention, the division of the phase containing the analyte is done without any liquid transfer other than the addition of the initial solution, and particularly without pipetting, which is always a source of inaccuracies, which furthermore are cumulative. No valves are necessary, and the device 1, 40 is simpler to manufacture, without considering the increase in precision inherent to the elimination of mechanical parts.

The system according to the invention may be designed with different sizes of receptacles and devices, varying from a few micrometers up to several centimetres. For example, for a device similar to that shown in FIG. 1, we could have:
Volume of first receptacle 10: 0.6 μl
Dimensions of the first receptacle 10:
4 mm×1.5 mm×0.1 mm
Volume of the second receptacle 12: 40 nl Dimensions of the second receptacles 12:
0.4 mm×1 mm×0.1 mm
Size of the connecting capillaries 14:
2 mm×0.1 mm×0.1 mm
Pitch between chambers: 500 μm
Total size of base 2: 6 mm×6 mm
Size of the magnet base: 8 mm×8 mm Another possibility for a base 2 with dimensions 8 mm×8 mm would be to have a magnet in which the dimensions of the main block are slightly larger than 8×8 mm.

Similarly, as described above, it is possible to have different sizes and shapes of magnets. Long magnets themselves may have different shapes, for example a parallelepiped shaped block, or a block with a pentagon shaped cross-section, or a triangle above a rectangle, and the triangle possibly being truncated.

The division device could form part of a wider assembly; it would then be possible to consider successive divisions of the initial sample, in which a second receptacle of a device is itself a first receptacle for another device following it, possibly with treatment of the sample between different successive divisions.

Finally, the same magnetic means can be used to control the division for a large number and a very large variety of devices 1, 40. For example for the first embodiment, any set of supports 2-6 with identical shape and size and for which the inlet chamber 10 is similar but for which the fluid circuits 14 are different, may be controlled by the same magnet.

Example of Use

A NASBA amplification with real time detection by a molecular marker can be installed in each reaction chamber 12. In this method of detection/analysis of nucleic targets present in solution, the sample has to be divided into several channels so as to be able to carry out a maximum number of tests in parallel.

The procedure then takes place as follows:
i. Targets to be amplified are captured on magnetic particles using conventional techniques; the number of capture probes fixed on the particles will be the same as the number of targets to be amplified, and complementary to these targets.
ii. A device like that shown diagrammatically in FIG. 1 is filled with an appropriate buffer, for example TE 1M NaCl or Triton X100 0.05%, at a temperature of about 30° C. During filling, air trapping chambers 8 present along capillaries 14 remain full of air.
iii. The sample is deposited in an inlet cone 4 of the device as shown in FIG. 1.
iv. Magnetic sedimentation, division and transport according to the invention are carried out, transport of the analyte displacing the analyte into the second chambers 12.
v. The amplification mix containing enzymes and specific primers is injected into each chamber, for example using syringe pumps. This injection is done through the end opposite the end in which the sample is added, in other words through the vents 18.
vi. The temperature of the device is then increased up to 42° C., and the system is allowed to incubate for 1 to 2 h, the fluorescence of the markers being read at regular time intervals for each reaction chamber 12.

Comparative Tests

Four types of device 60 were made as shown diagrammatically in FIGS. 7a-7d.

Figures 7A, 7B:
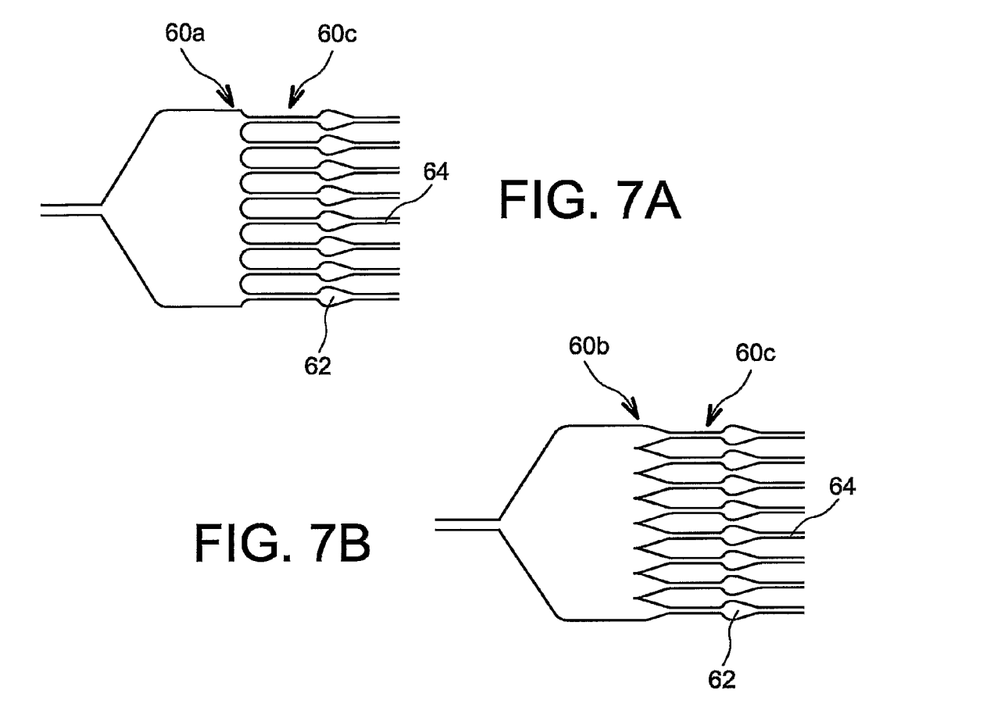
FIGS. 7a to 7d illustrate devices used when carrying out the tests.
Figure 7C:
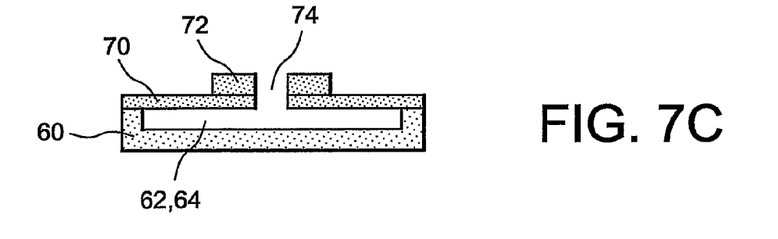

Chip types 60a, 60b and 60c shown in FIGS. 7a and 7b were made using the same deep etching in silicon technology followed by a thermal oxidation step.

Chips 60a and 60b are identical, the only difference being the design of the division comb, which is provided with teeth with rounded and pointed ends respectively. Chip type 60c has the same geometries, but with smaller dimensions, the surface of the receptacle 62 in which the magnetic residues are formed being divided by a factor of 3. In particular, the width of the teeth of the comb (in other words the pitch between the channels 64) is smaller, of the order of 500 µm for devices 60c compared with 900 µm for devices 60a and 60b.

Figure 7D:
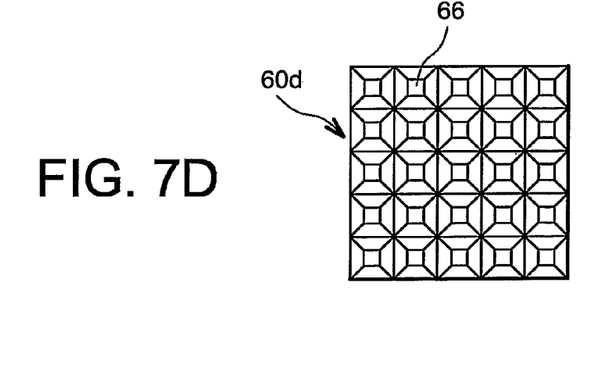

Devices 60d in FIG. 7d are made by anisotropic etching in a bath of KOH that forms dishes 66 with inclined sides.

Magnetic division experiments were carried out using devices 60 on which a PDMS cover 70 was glued. The shape of the cover was designed to be sufficiently thick to contain a 25 µl sample volume, in other words for example, particularly for devices 60a-60c, a plane cover 70 with uniform thickness except for a protuberance 72 located at the first receptacle (see FIG. 7c). The area 74 for injection of the sample was then opened with a scalpel blade so as to make a cut to prevent debris from being collected in the channels 64.

The magnetic particles were marked with fluorescent particles using a marking protocol using 605 Qdots (cat. #1000-1 by Quantum Dots Corp.) on Immunicon magnetic particles (No. F-3106) with a concentration of $7.5 \times 10^6$ Immunicon particles/µl with 10 Qdot/Immunicon in a 10 mM Tris buffer (pH=8:1M NaCl, Triton X100 0.05%, salmon DNA 0.14 mg/ml) so that the division could be quantified.

Depending on the geometry of the devices, the solution containing particles had different characteristics; for a component 60a with eight channels 64, 8 µl of solution containing particles and 17 µl of buffer were used; for a component 60d with 25 dishes, 25 µl of solution containing particles without any added buffer were used.

All measurements were made using a Zeiss Axioplan II microscope fitted with its type HBO 100/1007-980 illumination system comprising a mercury arc lamp type HBO 100W/2 and its power supply ebq 100. The 5×/0, 13HD-442924 and 10×/0, 20HD-442934 lenses and the fluorescein cube (optical filter assemblies) are used particularly for observation in black background and in epi-fluorescence. For imagery, the microscope was coupled to a Hamamatsu type ORCA Ergs HPF-C4742-80-12-AG camera, with its HPF-COMPX-SIMPLE-PCI acquisition software. All images were processed on the same AnalySIS software.

The Rolin magnet was used for devices 60a to 60c. A turned over APIS type magnet was used for device 60d, so as to obtain a uniform magnetic field with a plane base.

The operating method consisted of:
Pre-filling with buffer (devices 60a, 60b, 60c were placed in a vacuum chamber)
Placement and alignment of the magnet under the microscope.
Lower the magnet.
Put the device into place.
Fluorescence images of the bottom of each receptacle.
Injection of particles (8 residues in 25 µl buffer).
Reach equilibrium on some experiments.
Raise the magnet.
Monitor sedimentation in black light (for chip 60d, a microscope slide is placed on the component to prevent light reflection due to the meniscus).
Displacement of the device with respect to the magnet, and magnetic division.
Fluorescence images of each receptacle.

The fluorescence intensity for each residue is an integral intensity on a surface broadly encompassing the residue; it is obtained by subtraction of the intensity obtained before division from the intensity obtained after division, and therefore only represents the fluorescence intensity generated by marked magnetic particles. Coefficients of variation (CV) were calculated starting from the set of measurements (on the eight channels of devices 60a-60c), removing aberrant points if necessary (for example large external pollution particle).

The following table resumes the CVs obtained and the CV obtained on fluorescence measurements in channels filled with buffer only.

|  | device | CV before division (%) | CV after division (%) |
|---|---|---|---|
|  | 60b | 1 | 15 |
|  | 60c round | 1 | 13 |
|  | 60c pointed | 1 | 36 |
|  | 60c round | 2.4 | 5 |
|  | 60c pointed | 1.2 | 13 |
|  | 60c round | 1.2 | 5 |
|  | 60c pointed | 2 | 12 |
|  | 60a | 2 | 13 |
|  | 60d (9 dishes) | 0.6 | 38 |
| Sedimentation for 5 minutes | 60c round | 1 | 4 |
|  | 60c round | 2 | 5 |
|  | 60c pointed | 3 | 5 |
|  | 60c pointed | 5 | 3 |
|  | 60c pointed | 2 | 5 |
|  | 60c round | 1 | 5 |
|  | 60d (9 dishes) | 4 | 5 |
|  | 60d (25 dishes) | 16 | 20 |
|  | 60d (9 dishes) | 3 | 10 |
|  | 60d (25 dishes) | 10 | 18 |
|  | 60d (rows of 8 dishes) | 13 | 10 |

It should be noted that CVs on fluorescence measurements in components filled with buffer before the division are less than 5%, except for type 60d components with 25 dishes. CVs on fluorescence measurements after division are less than 5% on type 60c components when an equilibrium time is respected before sedimentation. This excellent result was obtained with chips for which the covers 70 (and particularly the opening 74 for injection of the sample) were cut out very approximately. Consequently, the geometric shape of the opening in the cover is not a critical parameter for making a good quality magnetic division with type 60c components. In the case of vertical sedimentation (type 60d components), the results are encouraging for matrices of 9 dishes (CV<10%).

Furthermore, fluorescence intensity profiles along the eight channels in type 60a-60c devices were studied; no effect due to the geometry of the injection area into the cover was noted.

No drop in the global fluorescence intensity was noted during a sequence including steps consisting of sedimentation, division, return of residues into the first receptacle, dispersion of the residue, sedimentation, division, regardless of the device 60; therefore there were no particle losses during the passage on the division comb. On the other hand, during these steps, the CV was degraded for type 60c components with a pointed comb, while it remained less than 5% for the rounded comb.

Having seen these results, it is quite obvious that the division method is efficient for equitable distribution of a set of magnetic particles into sub-sets. The main conclusions to be remembered are:
An equitable division between channels with a CV of less than 5% is achieved.
The loss of particles during division is negligible.

Division combs (60*a*, 60*b*, 60*c*) give better results than components for division by sedimentation in dishes (60*d*).

The geometry of the sample injection area has no significant influence.

A Brownian distribution step is preferable before sedimentation of particles.

The invention claimed is:

1. A method for dividing an analyte present in a solution comprising:
    disposing the solution including the analyte fixed to magnetic particles in a first receptacle;
    attracting, with a first magnetic mechanism, the magnetic particles fixed to the analyte to a bottom of the first receptacle and forming an initial residue forming a linear structure on the bottom of the first receptacle; and
    after forming the initial residue at the bottom of the first receptacle, dividing the initial residue into a plurality of residues by linearly displacing a second magnetic mechanism, which causes the initial residue to enter into fluid channels connecting the first receptacle to second receptacles, where each of the second receptacles is connected to the first receptacle through at least one of the fluid channels, and to divide said initial residue, by the fluid channels, into the plurality of residues, the displacing the second magnetic mechanism being such that the linear structure formed by the residues is maintained.

2. The method according to claim 1, wherein all of the fluid channels are parallel to each other, and the second magnetic mechanism is linearly displaced parallel to a direction of the fluid channels.

3. The method according to claim 1, wherein the initial residue is a single and linear-shaped residue, dividing the first receptacle into two parts.

4. The method according to claim 3, wherein each of the fluid channels is located on a same side of the initial residue in a direction of the linear displacement of the second magnetic mechanism.

5. The method according to claim 3, wherein the second magnetic mechanism includes a linear magnet.

6. The method according to claim 1, wherein the second magnetic mechanism includes a magnetic structure with multiple tips or pyramid shaped projections.

7. The method according to claim 1, wherein each of the fluid channels is a physical fluid channel that includes a magnetic strip.

8. The method according to claim 1, wherein each of the second receptacles is connected to the first receptacle through a single one of the fluid channels that includes a capillary.

9. The method according to claim 1, wherein the dividing includes dividing the analyte quantity into equal quantities in each second receptacle.

10. The method according to claim 1, wherein the attracting includes forming an agglomeration of the analyte fixed to the magnetic particles.

11. The method according to claim 1, wherein each of the fluid channels is a magnetic guide fluid channel that is formed by a magnetic strip.

12. The method according to claim 1, wherein each of the fluid channels is a physical fluid channel that has a capillary structure.

* * * * *